(12) United States Patent
Crispino et al.

(10) Patent No.: US 7,671,199 B2
(45) Date of Patent: Mar. 2, 2010

(54) PROCESS FOR THE PREPARATION OF [(1R), 2S]-2-AMINOPROPIONIC ACID 2-[4-(4-FLUORO-2-METHYL-1H-INDOL-5-YLOXY)-5-METHYLPYRROLO[2, 1-F][1,2,4]TRIAZIN-6-YLOXY]-1-METHYLETHYL ESTER

(75) Inventors: Gerard A. Crispino, Lawrenceville, NJ (US); Mourad Hamedi, Eatontown, NJ (US); Thomas L. LaPorte, Kendall Park, NJ (US); John E. Thornton, Newtown, PA (US); Jaan A. Pesti, Yardley, PA (US); Zhongmin Xu, Princeton, NJ (US); Paul C. Lobben, Lawrenceville, NJ (US); David K. Leahy, Hightstown, NJ (US); Jale Muslehiddinoglu, Hightstown, NJ (US); Chiajen Lai, Kendall Park, NJ (US); Lori Ann Spangler, Churchville, PA (US); Robert P. Discordia, Pennington, NJ (US); Francis S. Gibson, Pennington, NJ (US)

(73) Assignee: Britsol-Myers Squibb Company, Princeton, NJ (US)

( * ) Notice: Subject to any disclaimer, the term of this patent is extended or adjusted under 35 U.S.C. 154(b) by 91 days.

(21) Appl. No.: 11/737,787

(22) Filed: Apr. 20, 2007

(65) Prior Publication Data
US 2007/0249610 A1    Oct. 25, 2007

Related U.S. Application Data

(60) Provisional application No. 60/745,300, filed on Apr. 21, 2006.

(51) Int. Cl.
C07D 487/04    (2006.01)
A61K 31/53    (2006.01)
A61P 3/10    (2006.01)

(52) U.S. Cl. .................................... 544/183; 514/243
(58) Field of Classification Search ................. 544/183; 514/243
See application file for complete search history.

(56) References Cited

U.S. PATENT DOCUMENTS

| | | | |
|---|---|---|---|
| 6,869,952 B2 | 3/2005 | Bhide et al. | |
| 6,933,386 B2 | 8/2005 | Bhide et al. | |
| 6,982,265 B1 | 1/2006 | Hunt et al. | |
| 7,112,675 B2 | 9/2006 | Hunt et al. | |
| 2005/0288289 A1* | 12/2005 | Crispino et al. | 514/243 |
| 2006/0286646 A1 | 12/2006 | Patel et al. | |
| 2007/0088035 A1 | 4/2007 | Thornton | |

FOREIGN PATENT DOCUMENTS

| | | |
|---|---|---|
| WO | WO 2004/009601 | 1/2004 |
| WO | WO 2004/009784 | 1/2004 |

* cited by examiner

*Primary Examiner*—Venkataraman Balasubramanian
(74) *Attorney, Agent, or Firm*—Elliott Korsen (57) ABSTRACT

The invention relates to an improved process for preparing [(1R), 2S]-2-aminopropionic acid 2-[4-(4-fluoro-2-methyl-1H-indol-5-yloxy)-5-methylpyrrolo[2,1-f][1,2,4]triazin-6-yloxy]-1-methylethyl ester of the formula:

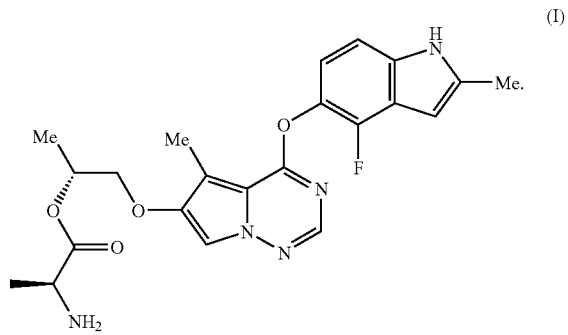

Compound I has been shown to be useful for the treatment of certain types of cancer.

16 Claims, 1 Drawing Sheet

FIG. 1

PROCESS FOR THE PREPARATION OF [(1R), 2S]-2-AMINOPROPIONIC ACID 2-[4-(4-FLUORO-2-METHYL-1H-INDOL-5-YLOXY)-5-METHYLPYRROLO[2,1-F][1,2,4]TRIAZIN-6-YLOXY]-1-METHYLETHYL ESTER

RELATED APPLICATION

This application claims the benefit of U.S. Provisional Application No. 60/745,300, filed Apr. 21, 2006, incorporated herein by reference in its entirety.

FIELD OF THE INVENTION

The invention generally relates to an improved process for the preparation of [(1R), 2S]-2-aminopropionic acid 2-[4-(4-fluoro-2-methyl-1H-indol-5-yloxy)-5-methylpyrrolo[2,1-f][1,2,4]triazin-6-yloxy]-1-methylethyl ester, a novel dual inhibitor of VEGFR and FGFR tyrosine kinases, currently in clinical trials for the treatment of cancer.

BACKGROUND OF THE INVENTION

There is disclosed an improved process for the preparation of [(1R), 2S]-2-aminopropionic acid 2-[4-(4-fluoro-2-methyl-1H-indol-5-yloxy)-5-methylpyrrolo[2,1-f][1,2,4]triazin-6-yloxy]-1-methylethyl ester, of formula I:

Compound I, compositions comprising Compound I, and methods of using Compound I are disclosed in U.S. Pat. No. 6,869,952 B2, which is assigned to the present assignee and is incorporated herein by reference in its entirety.

Compound I, a prodrug, is suitable for inhibiting tyrosine kinase activity of growth factor receptors such as VEGFR-2 and FGFR-1 and is useful in the treatment of cancer. Compound I is also useful in the treatment of diseases, other than cancer, which are associated with signal transduction pathways operating through growth factors and anti-angiogenesis receptors such as VEGFR-2.

SUMMARY OF THE INVENTION

One aspect of the invention provides an improved process for the preparation of Compound I, [(1R),2S]-2-aminopropionic acid 2-[4-(4-fluoro-2-methyl-1H-indol-5-yloxy)-5-methylpyrrolo[2,1-f][1,2,4]triazin-6-yloxy]-1-methylethyl ester, a novel VEGFR-2 inhibitor currently in clinical trials for the treatment of cancer.

A second aspect of the invention provides a process for the preparation of Compound C of the formula through a continuous oxidation and quench. The continuous process involves better heat transfer and the use of significantly less material in the reactor than a batch process to prevent potentially dangerous thermal runaway.

A third aspect of the invention provides an improved preparation and purification of Compound H, a key precursor of Compound I.

A final aspect of the invention provides a method for treating a proliferative disease, comprising administering to a mammalian species in need thereof, a therapeutically effective amount of Compound I, wherein Compound I is prepared utilizing the novel process steps of the invention.

The processes of the invention have several important advantages over prior syntheses of Compound I. In particular, due to the highly hazardous nature of some of the reactants, the continuous process developed is the safest way found to prepare intermediates for compound I on a commercial scale. Additionally, the process consistently provides Compound I in high quality for use as a pharmaceutical API.

BRIEF DESCRIPTION OF THE DRAWINGS

The invention is illustrated by reference to the accompanying drawings described below.

DETAILED DESCRIPTION OF THE INVENTION

The present invention provides an improved process for the preparation of Compound I, (I)

comprising the steps of
a) reacting Compound A of the formula

Compound A with a methylating agent, such as methylmagnesium chloride, in a suitable solvent to afford Compound B of the formula Compound B b) using a continuous oxidation and quench reaction to prepare Compound C of the formula Compound C from Compound B, and then protecting to convert Compound C to Compound D of the formula Compound D c) chlorinating Compound D to afford Compound E of the formula

Compound E d) which is coupled with Compound F of the formula

Compound F to afford Compound G of the formula

Compound G e) which is subsequently deprotected and reacted with (R)-(+)-propylene oxide in a suitable solvent, and optionally recrystallized to improve quality, to afford Compound H of the formula Compound H which is reacted with Cbz-L-alanine and a coupling reagent to afford Compound J of the formula Compound J which is deprotected and crystallized to afford crystalline Compound I, as Form N-1. Form N-1 of Compound I is described and claimed in U.S. Ser. No. 11/527,864, filed Sep. 27, 2006, the subject matter of which is hereby incorporated by reference.

Use and Utility

Compound I is useful for inhibiting protein kinases, such as, for example, VEGF. More specifically, Compound I inhibits the effects of VEGF and FGF which have been associated with angiogenesis and/or increased vascular permeability such as cancer. The invention also relates to a pharmaceutical composition comprising Compound I, and a pharmaceutically acceptable carrier or diluent; and to the use of this pharmaceutical composition in the treatment of hyperproliferative disorders in mammals. In particular, the pharmaceutical composition may be employed to inhibit the growth of those primary and recurrent solid tumors which are associated with VEGF and FGF, especially those tumors which are significantly dependent on VEGF for their growth and spread, including for example, cancers of the bladder, liver, squamous cell, head, colorectal, esophageal, gynecological (such as ovarian), pancreas, breast, prostate, lung, vulva, skin, brain, genitourinary tract, non-small cell lung cancer (NSCLC), lymphatic system (such as thyroid), stomach, larynx, and lung. In another embodiment, Compound I may also be useful in the treatment of non-cancerous disorders such as diabetes, diabetic retinopathy, psoriasis, rheumatoid arthritis, obesity, Kaposi's sarcoma, haemangioma, acute and chronic nephropathies, atheroma, arterial restenosis, autoimmune diseases, acute inflammation and ocular diseases with retinal vessel proliferation, diabetic retinopathy, retinopathy of prematurity and macular degeneration. Compound I possesses good activity against VEGF receptor tyrosine kinase while possessing some activity against other tyrosine kinases.

Compound I may also inhibit other receptor tyrosine kinases including FGFR, HER1 and HER2 and is therefore useful in the treatment of proliferative disorders such as psoriasis and cancer. The HER1 receptor kinase has been shown to be expressed and activated in many solid tumors including non-small cell lung, colorectal, and breast cancer. Similarly, the HER2 receptor kinase has been shown to be overexpressed in breast, ovarian, lung, and gastric cancer. Monoclonal antibodies that downregulate the abundance of the HER2 receptor or inhibit signaling by the HER1 receptor have shown anti-tumor efficacy in preclinical and clinical studies. It is therefore expected that inhibitors of the HER1 and/or HER2 kinases will have efficacy in the treatment of tumors that depend on signaling from either of the two receptors. The ability of Compound I to inhibit HER1 further adds to their use as anti-angiogenic agents.

The antiproliferative, antiangiogenic, and/or vascular permeability reducing treatment defined herein before may be applied as a sole therapy or may involve, in addition to Compound I, one or more other substances and/or treatments. Such conjoint treatment may be achieved by way of the simultaneous, sequential, or separate administration of the individual components of the treatment. Compound I may also be useful in combination with known anti-cancer and cytotoxic agents and treatments, including radiation. If formulated as a fixed dose, such combination products employ Compound I within the dosage range described below and the other pharmaceutically active agent within its approved dosage range. Compound I may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology, the other component(s) of such conjoint treatment in addition to the antiproliferative, antiangiogenic, and/or vascular permeability reducing treatment defined herein before may be: surgery, radiotherapy, or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, and razoxane);

(ii) cytostatic agents such as antiestrogens (for example, tamoxifen, toremifene, raloxifene, droloxifene, and iodoxifene), progestogens (for example, megestrol acetate), aromatase inhibitors (for example, anastrozole, letrozole, borazole, and exemestane), antihormones, antiprogestogens, antiandrogens (for example, flutamide, nilutamide, bicalutamide, and cyproterone acetate), LHRH agonists and antagonists (for example, gosereline acetate and leuprolide), inhibitors of testosterone 5α-dihydroreductase (for example, finasteride), farnesyltransferase inhibitors, anti-invasion agents (for example, metalloproteinase inhibitors like marimastat and inhibitors of urokinase plasminogen activator receptor function) and inhibitors of growth factor function, (such growth factors include for example, EGF, FGF, platelet derived growth factor and hepatocyte growth factor such as growth factor antibodies, growth factor receptor antibodies such as Avastin® (bevacizumab) and Erbitux® (cetuximab); tyrosine kinase inhibitors, and serine/threonine kinase inhibitors); and (iii) antiproliferative/antineoplastic drugs and combinations thereof, as used in medical oncology, such as antimetabolites (for example, antifolates like methotrexate, fluoropyrimidines like 5-fluorouracil, purine and adenosine analogues, cytosine arabinoside); intercalating antitumor antibiotics (for example, anthracyclines like doxorubicin, daunomycin, epirubicin, idarubicin, mitomycin-C, dactinomycin, and mithramycin); platinum derivatives (for example, cisplatin and carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine and taxoids like Taxol® (paclitaxel), Taxotere® (docetaxel) and newer microbtubule agents such as epothilone analogs, discodermolide analogs, and eleutherobin analogs); topoisomerase inhibitors (for example, epipodophyllotoxins like etoposide, teniposide, amsacrine, and topotecan); cell cycle inhibitors (for example, flavopyridols); biological response modifiers, and proteasome inhibitors such as Velcade® (bortezomib).

As stated above, Compound I is of interest for its antiangiogenic and/or vascular permeability reducing effects. This compound is expected to be useful in a wide range of disease states including cancer, diabetes, psoriasis, rheumatoid arthritis, Kaposi's sarcoma, haemangioma, obesity, acute and chronic nephropathies, atheroma, arterial restenosis, autoimmune diseases, acute inflammation and ocular diseases associated with retinal vessel proliferation such as diabetic retinopathy.

More specifically, Compound I is useful in the treatment of a variety of cancers, including (but not limited to) the following:
- carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;
- hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burkett's lymphoma;
- hematopoietic tumors of myeloid lineage, including acute and chronic myelogenous leukemias, myelodysplastic syndrome, and promyelocytic leukemia;
- tumors of mesenchymal origin, including fibrosarcoma and rhabdomyosarcoma;
- tumors of the central and peripheral nervous system, including astrocytoma, neuroblastoma, glioma, and schwannomas; and
- other tumors, including melanoma, seminoma, teratocarcinoma, osteosarcoma, xeroderma pigmentosum, keratoacanthoma, thyroid follicular cancer, and Kaposi's sarcoma.

Compound I is especially useful in treatment of tumors having a high incidence of tyrosine kinase activity, such as colon, lung, hepatocellular and pancreatic tumors. By the administration of a composition (or a combination) comprising Compound I, development of tumors in a mammalian host is reduced.

Compound I may also be useful in the treatment of diseases other than cancer that may be associated with signal transduction pathways operating through growth factor receptors such as VEGFR-2 and FGFR-1.

Compound I may be formulated with a pharmaceutical vehicle or diluent for oral, intravenous, or subcutaneous administration. The pharmaceutical composition can be formulated in a classical manner using solid or liquid vehicles, diluents, and/or additives appropriate to the desired mode of administration. Orally, Compound I can be administered in the form of tablets, including coated tablets, capsules, granules, powders, and the like. Compound I may also be administered as a suspension using carriers appropriate to this mode of administration.

The effective amount of Compound I may be determined by one of ordinary skill in the art, and includes exemplary dosage amounts for a mammal of from about 0.05 to about 300 mg/kg/day, preferably less than about 200 mg/kg/day, in a single dose or in 2 to 4 divided doses. In particular, a dose of 600-800 mg/day is preferred. It will be understood that the specific dose level and frequency of dosage for any particular subject may be varied and will depend upon a variety of factors, the bioavailability of Compound I in Form N-1, the metabolic stability and length of action of Compound I, the species, age, body weight, general health, sex, and diet of the subject, the mode and time of administration, rate of excretion, drug combination, and severity of the particular condition. Preferred subjects for treatment include animals, most preferably mammalian species such as humans and domestic animals such as dogs, cats, horses, and the like.

The process of the invention is disclosed in the following reaction scheme:

Compound J

Compound I

Generally, Compound A can be converted to Compound B by treatment with an methylating agent, such as a Grignard reagent, i.e., methylmagnesium chloride in a suitable solvent. Suitable solvents include ethereal solvents such as THF, methyl-THF, MTBE or diethyl ether. THF is the preferred solvent for the reaction. Compound A is disclosed in U.S. Pat. No. 6,982,265 and Compound B is disclosed in U.S. Ser. No. 11/165,875 filed Jun. 24, 2005.

Compound C is prepared from Compound B in a continuous oxidation that is one of the key steps of the invention. The oxidation reaction of Compound B to Compound C can be conducted in a batch or a continuous process. The reaction mixture has the potential for thermal runaway and a continuous process minimizes the amount of material at risk at any given time to minimize explosive impact, and offers more efficient heat transfer to minimize runaway potential. In general, continuous reactions can be conducted using a continuous flow stirred tank reactor or a plug flow reactor. Considering the nature of the reaction, conducting it in a continuous flow stirred tank reactor would require a higher concentration of hydrogen peroxide than for a plug flow reactor to obtain a product with the same quality. Also, plug flow reactors have much greater heat transfer than continuous flow stirred tank reactors. Consequently, for reasons of safety and product quality, a plug flow reactor and a continuous process is the preferred mode to carry out the oxidation of Compound B to Compound C.

Figure 1:
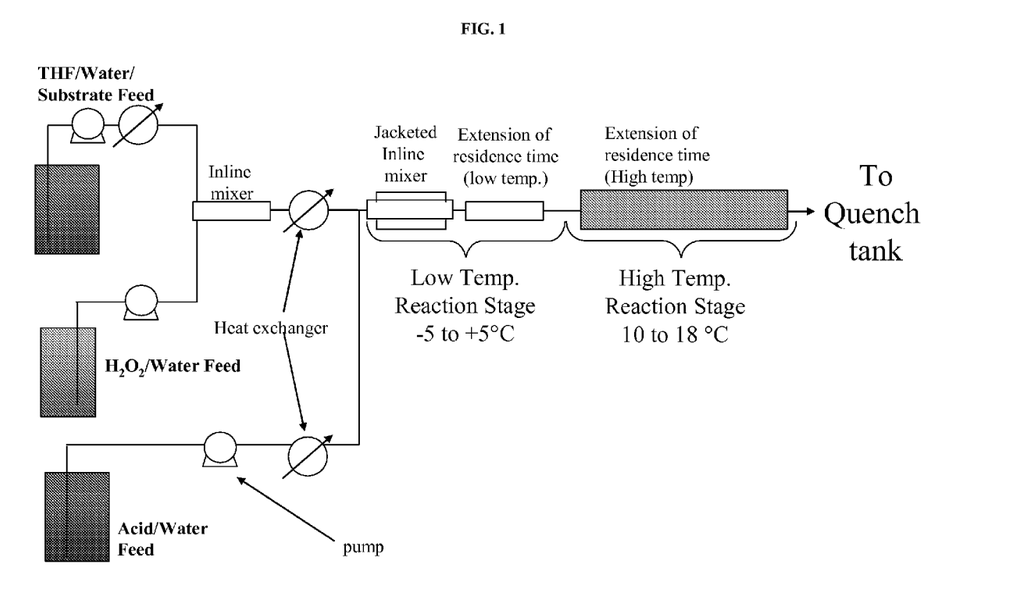
FIG. 1 shows the oxidation reaction and general setup for step 2.

In this step, a solution of compound B(in THF and water) and hydrogen peroxide is mixed and cooled. An acid is added to the reaction mixture and the reaction stream goes into what will be referred to as the Low Temperature Reaction Stage. This generally takes place at a temperature of about 0° C. (−5 C to 5C). Next the reaction mixture flows into the High Temperature Reaction Stage, which is kept at a temperature of about 10° C. to about 18° C. A preferred temperature for this stage is about 14° C. The relative flow rates of the 3 input streams are adjusted to control reaction stoichiometry and product quality. The flow rates and temperature range of the continuous process are controlled in such a way that the total residence time in the continuous reactor is 12-18 minutes. Finally, the desired compound flows into a quenching tank where it can be treated in a number of ways prior to being used in the next step. Preferably, the hydrogen peroxide excess is quenched with a reducing agent and the pH is adjusted. The continuous output stream can be directed to a single quench tank for a period of 4-30 hours.

A key to the process is that Compound C, which is disclosed in U.S. Ser. No. 11/165,875 filed Jun. 24, 2005, is not isolated. The quenched stream is protected to form Compound D, which is also disclosed in U.S. Ser. No. 11/165,875 filed Jun. 24, 2005, using pivaloyl chloride and an amine base.

In the next step of the process, Compound D is chlorinated utilizing phosphorus oxychloride to afford Compound E. Compound E is also disclosed in U.S. Ser. No. 11/165,875 filed Jun. 24, 2005.

In the preparation of Compound G from Compounds E and F, generally Compound F is activated by mixing with a base such as DABCO, then combined with Compound E to form Compound G. The preparation of Compound F is disclosed and claimed in U.S. Pat. No. 6,933,386. Compound G can be optionally purified by recrystallization from acetone/water.

Compound H can be prepared from Compound G through intermediate K using a number of reagents to effect the deprotection of Compound G. These include NaOMe, KOMe, KOEt, KOiPr, NaOEt, and NaOiPr. NaOMe is the preferred reagent. In place of acetonitrile, other solvents such as methanol, ethanol, iso-propanol, DMF and THF can be employed. Additionally, other solvent combinations able to effect the coupling reaction of Compound K with propylene oxide include acetone and water or methanol and water, although neither solvent combination provides the high yield and purity of the acetonitrile/water combination shown in the scheme.

Optionally, Compound H can be recrystallized from either acetone/water or acetonitrile/water to afford high quality Compound H. Acetone/water is preferred.

The final step, the preparation of Compound I from Compound H, involves the ester formation between Compound H and CBz-L-alanine, using a coupling agent to afford Compound J. Compound J is generally not isolated. This reaction generally takes place in THF or ethyl acetate with added DMF at 0° C. to room temperature. The preferred coupling agent is EDAC-HCl (N-(3-dimethylaminopropyl)-N'-ethylcarbodiimide hydrochloride). In a second phase of this step, Compound J is deprotected, through hydrogenation, and crystallized to afford Compound I.

Generally, Compound I can be crystallized by treatment with heptanes and washing with ethyl acetate/heptanes and THF/heptanes.

Other solvents that have been used successfully with the preferred reaction conditions and the alternative reagents mentioned above include alkyl acetates, such as EtOAc, nBuOAc, and iPrOAc; ethers, such as THF and 2-methyl THF; halogenated solvent such as dichloromethane and polar aprotic solvents such as DMF and NMP. These are also useful as co-solvents.

Other suitable solvents for crystallization includes a variety of alkyl acetates, such as nBuOAc, iBuOAc, iPrOAc, and ethers such as THF. Solvents that have been demonstrated as antisolvents are: n-heptane, heptanes, toluene, MTBE. Other solvents such as methylene chloride, cyclohexane, acetone, isopropyl alcohol, NMP, DMF, DMA can potentially be used in the crystallization of I. Crystallization conditions can also be varied in terms of temperature, concentration, seeding strategy, heating/cooling profile, and agitation rates.

EXAMPLES

The invention will now be further described by the following working example(s), which are preferred embodiments of the invention. All temperatures are in degrees Celsius (° C.) unless otherwise indicated. These examples are illustrative rather than limiting and it is to be understood that there may be other embodiments that fall within the spirit and scope of the invention as defined by the claims appended hereto.

Example 1

Conversion of Compound A to Compound B

A mixture of compound A (22.0 kg, 99.5 mole) and dry tetrahydrofuran (257.3 kg) was purged with nitrogen and cooled to 7° C. A solution of methylmagnesium chloride in tetrahydrofuran (3M, 169.4 kg, 503.1 mole) was added over 25 min at 6-12° C. followed by tetrahydrofuran (2 kg) to wash out the line. The solution was warmed to 28° C./10 min and maintained at about 30° C. for another 2 h. The reaction mixture was transferred into a solution of ammonium chloride (75.9 kg) in water (303 kg) over 3 hours and 20 minutes at 0-4° C. The reaction vessel was rinsed with another 22 kg of tetrahydrofuran, and ethyl acetate (237.7 kg) was added to the mixture. The phases were allowed to settle for 1.5 h and 750 L of the upper organic phase was recovered. The organic phase was washed with a solution of sodium chloride (24 kg) in water (83.6 kg), and filtered through a pad of Celite (11 kg) to produce 750 L of filtrate. The filtrate was distilled under vacuum to 160 L. Ethyl acetate was charged and the distillation repeated down to 160 L. This cycle was repeated with 49.6 kg ethyl acetate. The mixture was diluted with 60.7 kg of heptane and the distillation repeated. The crystallizing mass was maintained at 31° C. for 1 h and cooled to 2° C. over 4 h. The crystals were collected by filtration and washed with a solution of ethyl acetate (22 kg) and heptane (11.8 kg). Once the cake had deliquored, it was dried at 35° C. under vacuum over 3 days to provide 19.6 kg of 92 wt % Compound B (87.5% yield).

Example 2

Example 2A

Reverse Quench with Variable pH

Three feed solutions are prepared and used for the reaction in converting Compound B to Compound C through a continuous oxidation process. A mixture of compound B (120 g) plus tetrahydrofuran (1452.15 g) and water (245.66 g) is first prepared. This solution is referred to as the starting material solution (SMS). The other two feed solutions which are needed for the reaction are: commercial 70% (aqueous) methanesulfonic acid (MSA) and commercially available 50% (aqueous) hydrogen peroxide. The SMS stream is pumped through the system with a flow-rate of 31.9 grams/hour. The SMS is first pre-cooled to 0° C. through a heat exchanger and then mixed with the hydrogen peroxide solution which is being pumped through the system at a flow-rate of 6.1 grams/hour. The mixing takes place in an in-line mixer (microreactor or static mixer). The resulting mixture is then cooled to 0° C. through a heat exchanger and mixed in-line with the pre-cooled (0° C.) solution of methanesulfonic acid in a jacketed microreactor or static mixer. The flow rate of the methanesulfonic acid solution is 17.5 g/h. The mixing sequence is important in this process. Also, the relative flow-rates of each feed solution influences the reaction time and the product quality. To insure that the reaction temperature is controlled to alleviate any risk of a runaway reaction, while still allowing for complete reaction in a reasonable time frame, the reaction stream flows through two temperature zones. The first temperature zone has a range of −5 to 5° C. The residence time in this low temperature zone is approximately two minutes (including the in-line mixer). The second temperature zone has a residence time of ten to twelve minutes and a temperature of range of approximately 10-18° C.

The reaction stream exiting the continuous process is acidic and contains an excess of hydrogen peroxide. The output of the continuous reaction is directed to a quench tank. In this run, the quench tank is initially charged with 216.4 grams of sodium bisulfite ($NaHSO_3$), 517.06 grams of water and 296.34 grams of 28% aqueous ammonium hydroxide ($NH_4OH$). The quench tank solution is kept at 5-18° C. The initial pH of the quench solution is 10.7. The continuous reaction and quench are run for twenty four hours. At the twenty third hour of the run, the pH in the quench tank is about 6.23 and is then adjusted up to 7.3 with the addition of 12.62 grams of 28% ammonium hydroxide. At the end of the run the pH is adjusted to 7.1 with the addition of 4.19 grams of ammonium hydroxide. The organic and aqueous phases in the quench tank are separated and 624.06 grams of organic solution are recovered. The aqueous phase is washed with 208 grams of THF. The combined organic phases amount to 859.21 grams and the yield of the process is estimated to be 86%.

Example 2B

Reverse Quench with pH Control

The reaction conditions are the same as above but at a larger scale, and the quenching procedure is different. The three feed solutions are of the same composition. Feed rates are 52.1 g/min for the starting material solution, 9.91 g/min for the aqueous hydrogen peroxide, and 27.9 g/min for the aqueous methanesulfonic acid solution. Commercially available 50% by weight aqueous hydrogen peroxide is used. Methanesulfonic acid is prepared as a mixture of 9.18 kg of water and 22.776 kg of 99% methanesulfonic acid. The SMS is prepared with a mixture of 42.35 kg of tetrahydrofuran (THF), 7.00 kg of water and 3.495 kg of Compound B.

An alternative quench procedure was used in this example. The quench tank is initially charged with 15.580 kg of sodium bisulfite, 41.155 kg of water and 22.302 of 28% ammonium hydroxide. The initial pH of the solution is 7.6. The continuous process is run for 16 hours. The pH of the quench tank is continuously adjusted through out the run to be in the range of 6.3 to 8.5 by the addition of 28% ammonium hydroxide, as needed. During the run, the quench tank temperature was in the range of 5 to 18° C.

After the run is completed, the aqueous and organic phases are separated and the aqueous phase (129.8 kg) is washed with tetrahydrofuran (18.6 kg). Upon extraction and separation of the phases, the aqueous phase is discharged to waste and the lean organic phase (24.1 kg) is combined with the rich organic phase (39.7 kg). The estimated yield of Compound C is 82%.

Example 3

Synthesis of Compound D from Compound C in aqueous THF

An aqueous THF solution of Compound C (4005 kg solution, 132.9 kg Compound C by HPLC assay) was filtered through 10 micron polypropylene cloth to remove any residual solids. The volume was reduced by 60% via vacuum distillation to 7-8 w/w % Compound C by HPLC analysis. A test for pH indicated the solution was in the desired range of 7.0-7.5. Water content by KF titration found the solution to be within the desired 20-25 w/w % water range. The solution was cooled to 5° C., then triethylamine (242.9 kg) was added over 30 minutes. Trimethylacetyl chloride (169.1 kg) was added over 30 minutes, resulting in a mild exotherm. The reaction was deemed complete after 30 minutes by HPLC analysis.

The biphasic mixture was warmed to 20° C., held without stirring for 2 hours, then the spent aqueous lower layer was separated and discarded. The upper layer was concentrated via vacuum distillation (40° C.) during which time the product crystallized. The slurry was then diluted with water (1323 kg), cooled to <10° C. for two hours, filtered, and washed with water (600 L) three times. The white crystalline powder was dried under vacuum at 75° C. for 18 hours. Yield was 173.8 kg Compound D, 85.1% based on assay of the Compound C input solution. Purity was 98.2 w/w % by hplc analysis.

Example 4

Example 4A

Preparation of Compound G from Compound D and Compound F

Compound D (119.8 kg, 98.2 wt % pure, 472 mole) in dry acetonitrile (287 kg, 0.02% water) was placed under a nitrogen atmosphere and phosphorous oxychloride (148 kg, 966 mole) was added. Diisopropylethylamine (62.2 kg, 481 mole) was added over 15 minutes and the mixture was heated to reflux over 45 min. Once the reaction to convert Compound D to Compound E was complete, half of the reaction mass was transferred to a quench solution of 12.4 wt % aqueous dipotassium hydrogen phosphate solution (1950 kg) and isopropyl acetate (501 kg) over 1 h at 12-21° C. The second half was quenched similarly in a second vessel. The quenched solutions were stirred for 1 h, allowed to settle for 1-2.5 h and separated. The organic phases were combined. The combined solutions were washed with 15 wt % aqueous dipotassium hydrogen phosphate solution (537 kg) for 15 min followed by 80 min of settling before separation to produce a final pH of 8.3.

In another vessel, Compound F (87.4 kg, 98.7 wt % pure, 522 mole) was dissolved into acetonitrile (150 kg) and passed through a 1 micron filter to retain particulates. Additional acetonitrile (30 kg) was used to wash the remaining amounts. 1,4-Diaza-bicyclo[2.2.2]octane (59.4 kg, 530 mole) was charged to the solution followed by more acetonitrile (50 kg). To this mixture was added the solution of Compound E, through a filter, over 35 min. The residual amounts were transferred with more acetonitrile (71 kg). The mixture was stirred for 65 min and concentrated by distillation at 200 mBarr to 960 L, at which point the volume was maintained at ~1000 L by the addition of acetonitrile. The solvent exchange was halted after a total of 8¾ h when the isopropyl acetate content by GC was measured as 1.1 vol %. The mixture was cooled to 40° C. and 5° C. water (1200 L) was added over 1 h. The mixture was stirred 2 h and collected by filtration in a filter drier. The vessel contents were washed over with water (200 L), the cake was deliquored, and washed with water (3×450 L). The cake was dried at 75° C. (jacket) with occasional stirring once the loss on drying (LOD) value was <25%. The cake was dried until the LOD reached 0.3% to give 180.2 kg cream colored solids (98.8 wt%, 95.2% yield).

Recrystallization of Compound G from Aqueous Acetone (Optional)

A mixture of Compound G (254 kg solvent-wet compound, LOD=19.7%) in acetone (1500 kg) was stirred at 55-60° C. for 1 h to form a clear solution. The solution was cooled to 40-45° C. and was clarified by passage through a 10 μm filter over 45 min. The reactor was rinsed with more acetone (176 kg) and the combined solution was concentrated by the vacuum distillation of 645 kg acetone. The solution was cooled to 20° C. and water (840 kg) was added over 36 min. The resulting slurry was cooled to 0-5° C. and held for 2 h. The solids were collected by filtration over 80 min and washed with water (390 kg). This produced 284 kg of moist crystals that were dried under vacuum at 75° C. to produce 199.4 kg (98% recovery; 99.91 LC area % purity; <0.05% LOD; 0.07% water).

Alternate Preparation

Example 4B

Preparation of Compound G from Compound D and Compound F Via the Use of Sodium Dithionite Workup

Compound D (10.00 g, 99.3 wt % pure, 39.8 mmole) in dry acetonitrile (36 mL, <100 ppm water) was placed under a nitrogen atmosphere and phosphorous oxychloride (12.3 g, 99 wt %, 79.4 mmole) was added in one portion. Diisopropylethylamine (5.1 g, >99 wt %, 39.5 mmole) was added over 4 min and the mixture was heated to reflux over 30 min. After 10 hours of reflux and 9 hours of cooling, the solution of Compound E was transferred into a quench solution of 12 wt % aqueous dipotassium hydrogen phosphate solution (349 g) and isopropyl acetate (76 mL) at 5° C. The quenched mixture was stirred for 10 min, allowed to settle for 15 min and separated. The organic phase was washed with 15 wt % aqueous dipotassium hydrogen phosphate solution (49 g) for 1 min followed by 15 min of settling before phase separation (final pH=9).

In another vessel, Compound F (7.27 g, 99 wt % pure, 43.6 mmole) was dissolved into acetonitrile (24 mL) over 30 min and passed through a Whatman #4 paper filter. Additional acetonitrile (4 mL) was used to rinse the paper. 1,4-Diazabicyclo[2.2.2]octane (4.89g, 98 wt %, 42.7 mmole) was charged to the solution. After 25 min, the solution of Compound E was added to this slurry through a Whatman #4 paper filter, over 5 min. The residual amounts were transferred with more acetonitrile (3 mL). The mixture was stirred for 18 h and concentrated by distillation at 200 mBarr down to 100 mL, at which point the volume was maintained by the addition of acetonitrile. The solvent exchange was halted after 3.5 h when a total of 365 mL of distillate had been collected. The level was reduced to ~80 mL at this point. The mixture was cooled to 40° C. and 10 mL of tetrahydrofuran was charged followed by sufficient acetonitrile to restore the 100 mL level of slurry. This mixture was charged with 1.60 mL of a freshly prepared solution of sodium dithionite in water (100 mg/2.00 mL water). The mixture was brought to reflux over 10 min. After 30 min of reflux, an additional 1.60 mL of freshly prepared sodium dithionite solution was charged. After another 15 min, water (1.00 mL) was charged and the reflux maintained for an additional 5 min to dissolve additional solids. The solution was allowed to cool to 30° C. over 100 min. Water (100 mL) was added over 105 min and the slurry was stirred for 2.5 days. The crystals were collected by filtration in a Buchner filter on Whatman #4 paper and washed with water (4×38 mL). The cake was dried at 1 mmHg vacuum for 2 h to give 15.39 g of Compound G as a solid, (99.93 LC area % purity, 98% as is yield). This material contained 20-100 ppm of Compound D and 5-20 ppm of Compound E This material was optionally recrystallized from aqueous acetone. A mixture of Compound G (15.00 g) in acetone (90 mL) at 45-55° C. was clarified through Whatman #4 paper and washed through with another 5 mL acetone. The precipitated solids were redissolved by heating to reflux under nitrogen. The solution was cooled and seeded until nucleation had commenced. Crystal growth was allowed to proceed while cooling slowly over 17 h after which water (62 mL) was charged over 105 min. After 3 h, the solids were collected on Whatman #4 paper, washed with water (40 mL), and dried on the filter under a nitrogen blanket to remove the major portion of solvent. The crystals were dried further at 1 mmHg vacuum for 24 h to produce 14.24 g of crystals (97% recovery; 99.94 LC area % purity). This purified Compound G contained 5-20 ppm of Compound D and <5 ppm of Compound E Example 5

Preparation of Compound H from Compound G and Propylene Oxide

-continued

Compound H

Deprotection of Compound G to Afford Compound K

A jacketed 4000L-reaction vessel was equipped with a mechanical stirrer, reflux condenser, and temperature thermocouple. To the nitrogen swept reactor was charged acetonitrile (188.9 kg), followed successively by Compound G (170.8 kg, 430.8 mol), and acetonitrile (103 kg). The reaction mixture was cooled to 10° C. under a sweep of nitrogen. A 25 wt % solution of sodium methoxide in methanol (91.5 kg, 430.8 mmol) was added slowly to the reaction mixture, followed by a rinse of acetonitrile (28 kg) while maintaining the internal temperature under 23° C. The reaction mixture was stirred under nitrogen for 1 hour, at which time HPLC analysis of the reaction aliquot indicated complete consumption of Compound G.

Akylation of Compound K to Afford Compound H

Water (854 kg) was charged to the solution of Compound K followed by (R)-(+)propylene oxide (128.7 kg, 2218.4 mole) and acetonitrile rinse (22 kg). After the vent of the reaction vessel was closed, the resulting mixture was held at 20-30° C. for 17 hours to result in a slurry. At that time HPLC analysis of the reaction aliquot indicated a >98% of conversion to Compound H.

The slurry mixture was filtered in a filter-dryer through 20 μm filter-cloth under 30 psi pressure of nitrogen. The product cake was washed with a 20% aq. acetone solution, and a typical LOD of 25-35% resulted after complete deliquoring.

To the filter-dryer, a pre-mixed acetone/water solution (729 kg acetone/92.4 kg water) was charged to result in a slurry. The slurry was heated to 50-58° C. and stirred at this temperature for 20-90 min to give a solution, which was transferred to a jacketed 4000 L reaction vessel. The filter-dryer was rinsed with a pre-mixed acetone/water solution (182 kg acetone/23.1 kg water), and the rinse solution was combined with the dissolution solution. The combined solution was heated to 50-58° C. Water (1039.6 kg) was added over 50 min while keeping the internal temperature between 50-56° C. The resulting slurry was cooled to 18 -20° C. over 2 hours and aged for 6-20 hours. The solids were isolated by filtration in a filter-dryer. The wet cake was washed with a pre-mixed acetone/water solution (1366 kg water and 266 kg acetone), and dried at 50-60° C. under vacuum to afford 120 kg (75%) of Compound H.

Example 6

Example 6A

Preparation of Compound I from Compound H and CBz-alanine Structure of Compound H was Cut Off Funny in the Copy You Sent Compound H Compound J Compound I Conversion of Compound H to Compound J A 1000 gallon glass lined reactor was inerted three times with nitrogen, then was charged with 557.1 kg of THF followed by 73.7 kg of DMF. To this was charged 77.4 kg of Compound H, 60.2 kg of EDAC-HCl, and 0.760 kg 4-dimethylaminopyridine. The reaction was cooled to −1.7 to 2.7° C. Upon reaching the set temperature, 60.8 kg of CBz-L-alanine was charged followed by 65.0 kg of a THF rinse. The reaction was aged for 3 hours at which time a sample was taken and HPLC analysis indicated that no Compound H was detected. After 20 minutes, the reaction was quenched by charging 878.7 kg of 0.5M phosphoric acid in 18 wt % brine solution, follow by a rinse of 39.4 kg of water. The mixture was allowed to warm to room temperature and then agitated for 30 minutes. Agitation was stopped and the two phases were allowed to separate over 30 minutes. The spent lower aqueous was transferred to waste. The organic phase was washed with 880.3 kg of 5 wt % $K_2CO_3$ in 18 wt % brine solution. The mixture was agitated for 30 minutes, agitation was stopped and the two phases were allowed to separate over 30 minutes. The spent lower aqueous was transferred to waste. The organic phase was washed a second time with 506.4 kg of 5 wt % $K_2CO_3$ in 18 wt % brine solution. The mixture was again agitated for 30 minutes, then agitation was stopped and the two phases were allowed to separate over 30 minutes. The spent lower aqueous was transferred to waste.

The rich organic stream was held overnight. The next day the rich organic stream was concentrated from an initial volume of 540 L to a final volume of 295 L (jacket temperature <80° C., 200 mbar). Ethyl acetate was transferred from another reactor until the volume was adjusted to about 475 L. The solvent was switched to ethyl acetate via distillation. The stream of Compound J in ethyl acetate was filtered through a 10 micron polish filter and drummed resulting in 425.1 kg of a 26.6 wt % Compound J in ethyl acetate stream. The reactor was charged with 50.3 kg of an ethyl acetate rinse, then the rinse was passed through the polish filter and drummed separately. This corresponds to 114.28 kg of Compound J (92.7 % step yield).

Deprotection to Afford Compound I

Compound J as a solution in EtOAc (total 467 kg stream, containing 120 kg of Compound J) was added to a 250-gallon nominal size stainless steel reactor. The line was rinsed with 25 kg of EtOAc which was then followed by addition of 5% Pd/C (24 kg, 50 wt % water) and potassium carbonate (20 kg) to the reactor. The concentration was adjusted to 5 L/kg of Compound J by charging about 80 kg of EtOAc. The reactor was purged three times with nitrogen to a pressure of 30 psig, and twice with hydrogen to a pressure of 20 psig. The batch temperature was set to 25° C. The reaction mixture was agitated under an atmosphere of hydrogen at 20 psig for 7 hours. The reaction mixture was sampled; HPLC analysis indicated 99.45 % conversion. The vessel was depressurized, and purged with nitrogen. Compounds J and I and $CO_2$ by-product were monitored by in-line FTIR throughout the reaction and $CO_2$ was monitored during nitrogen purges in order to ensure that no $CO_2$ remained in the reaction solution. The reaction mixture was filtered through 5 micron bag filter followed by 3 micron sparkler and then 0.5 micron Cuno filter. The spent solids were washed with 180 kg of fresh EtOAc. The combined organic streams were assayed by HPLC to indicate an in-process yield of 80.98 kg, (88% yield based on compound H input).

Crystallization and Isolation of Compound I

Example A

Crystallization from EtOAc/Heptanes

Compound I as a solution in EtOAc (713.4 kg, 11.6wt %) was charged to a jacketed 2000L reactor equipped with mechanical stirrer, reflux condenser, and thermocouple. With the jacket temperature set at about 50° C., the solution was distilled under reduced pressure (about 200 mbar) to a concentration of approximately 20 wt %. Upon reaching the approximate concentration the distillation was switched to constant volume distillation, with fresh EtOAc being fed from a 4000 L reactor. About 400 kg of EtOAc was used for the constant volume distillation to afford a final solution concentration of 18.9 wt % Compound I. During distillation the batch temperature was maintained between 30-40° C.

Upon completion of distillation, the vacuum was released and the solution was warmed to about 45-50° C., and a clear solution was obtained. To the solution was added 275.0 kg of heptanes over 20-30 minutes while still maintaining the batch temperature at 40-50° C. Treating the reaction mixture with 0.3 kg of seeds and aging the mixture for 10 minutes afforded a stirrable slurry. An additional 275.0 kg of heptanes was added over 20-30 minutes. The resulting slurry was cooled to 20° C. over 2 hours and aged for an additional hour. The slurry was subjected to wet-milling for about 30 minutes to afford material of particle size less than 120μm. The solids were isolated by centrifuge operating at 500-700 rpm. The resulting wet cake was washed successively with about 300 kg of EtOAc/heptanes (1:4 v/v) and about 300 kg of heptanes, and dried at 50° C. under vacuum in a conical dryer to afford 69.9 kg of Compound I (~84.1% yield).

Example B

Crystallization of Compound I from BuOAc/Heptane

Compound I, as a solution in BuOAc (~150 kg, ~18 wt %) in a jacketed 2000 L reactor equipped with mechanical stirrer, reflux condenser, and thermocouple, was heated to about 60° C., and a clear solution was obtained. 40.9 kg of heptane was charged to the 2000 L reactor over 25 minutes to make the solution a supersaturated solution. The batch temperature was maintained at close to 60° C. during the heptane charge and 50 g seeds, dispersed in 0.7 kg n-heptane, was charged to the reactor through seeder to initiate crystallization. After the first heptane charge, the batch was cooled to 50-55° C. over 30 minutes and maintained at the same temperature for ½ hour. A slurry was established during the cooling and aging period. After aging, an additional 98.0 kg of n-heptane was charged to the reactor over 2 hours. The batch was then cooled to 15-20° C. over 2 hours and then held at 15-20° C. for 1 hour. The resulting slurry was subjected to wet milling with the wet-mill set up in a recirculation loop of the 2000 L reactor, located between the bottom valve and a diaphragm pump. The slurry was milled for approximately 4.5 hours until the particle size of the material is within the specification.

The slurry was filtered through a filter dryer with an effective filtration area of ~0.6 $m^2$. The isolated wet cake was then washed with about 34.3 kg of BuOAc/n-heptane (¼) mixture, and 58.9 kg of n-heptane. The wet cake was dried in-situ at 20° C. for 10 hours (with vacuum), followed by 50° C. vacuum drying for 2 hours. 19.3 kg of dry Compound I was discharged from the filter dryer, affording an overall yield of 69.3% from compound H.

Example 6B

Alternate Process

Conversion of Compound H to Compound J

A 2000 gallon glass lined reactor was inerted three times with nitrogen, and charged with 1056.7 kg of THF followed by 140.9 kg of DMF. To this mixture was charged 147.9 kg of Compound H. 115.9 kg of EDAC-HCl and 1.46 kg of 4-dimethylaminopyridine were charged and the reaction mixture was cooled. Upon reaching the desired temperature of less than 5° C., 116.8 kg of CBz-L-alanine was charged followed by 132.6 kg of THF as a rinse. The reaction was aged for 3.5 hours at which time a sample was taken. HPLC analysis indicated that less than 0.10% of Compound H was present. After an additional hour, the reaction was quenched by charging 1253.8 kg of 0.5M phosphoric acid in 15 wt % brine solution, followed by a rinse of 44.4 kg of water. The mixture was allowed to warm to room temperature with moderate agitation, and then aged for an additional 30 minutes. Agitation was stopped and the two phases were allowed to separate over 30 minutes. The spent lower aqueous was transferred to waste. The organic phase was subsequently washed with 1684.9 kg of 4 wt % $K_2CO_3$ in 15 wt % brine solution. The mixture was agitated for 30 minutes, agitation was stopped and the two phases were allowed to separate over 60 minutes.

The spent lower aqueous was transferred to waste. The organic phase was washed with 1825.7 kg of 15 wt % brine solution. The mixture was again agitated for 30 minutes, then agitation was stopped and the two phases were allowed to separate over 120 minutes. The spent lower aqueous was transferred to waste. The rich organic stream was concentrated from an initial volume of 897 L to a final volume of 526 L under atmospheric pressure. Subsequent constant volume distillation to a Karl-Fischer (KF) endpoint of 0.5 wt % was achieved using 902 kg of THF transferred from an additional vessel. The stream of Compound J in THF was filtered through a filter and drummed resulting in 1018.5 kg of Compound J in THF stream. The reactor was rinsed with 98.5 kg of a THF; the rinse was passed through the filter and drummed separately. Quantitative yield of the rich organic stream was determined by HPLC.

Deprotection to Afford Compound I

Compound J as a solution in THF (total 472 kg stream, containing 112 kg) was added to a 250-gallon nominal size stainless steel reactor, then followed by addition of 5% Pd/C (11.5 kg, 50 wt % water) to the reactor. The concentration was adjusted to 5 L/kg of Compound J by charging an additional 58 kg of THF. The reactor was purged three times with nitrogen to a pressure of 30 psig, followed by three hydrogen purges of the headspace cycling between 10 and 20 psig, under minimum agitation. The batch temperature was set to 25° C. The reaction mixture was agitated under an atmosphere of hydrogen fed by subsurface addition at 20 psig for 85 minutes. The initial pressure setpoint was at 25 psig to account for the rapid consumption of gas. The reaction mixture was sampled; HPLC analysis indicated 99.9% conversion. The vessel was depressurized, and purged with nitrogen. Compounds J and I and $CO_2$ by-product were monitored by in-line FTIR throughout the reaction and $CO_2$ was monitored during nitrogen purges in order to ensure that no $CO_2$ remained in the reaction solution. The reaction mixture was filtered through 1 micron bag filter followed by two in-series 0.5 micron polypropylene filters. The combined organic streams (598.6 kg, 15.0 wt %) were assayed by HPLC to indicate quantitative in-process yield based on compound H input).

Crystallization and Isolation of Compound I

Crystallization from EtOAc/Heptanes

Compound I as a solution in THF was charged to a jacketed 4000 L reactor equipped with mechanical stirrer, reflux condenser, and thermocouple to afford 1233.9 kg (including rinses) as a 13.9 wt % solution. With the jacket temperature set at about 80° C., the solution was distilled under reduced pressure (about 200 mbar) to a minimum volume of approximately 560 L. Subsequent constant volume distillation and solvent swap to EtOAc occurred with the following endpoints 4.2 vol % residual THF and a concentration of compound I of 21 wt % in EtOAc. During distillation the batch temperature was maintained between 20-40° C.

Upon completion of distillation, the vacuum was released and the solution was warmed to about 50-55° C. To the solution was added 459 kg of heptanes over 40 minutes while maintaining the batch temperature at 50-55° C. Treating the resulting clear solution with 0.6 kg of Compound I seeds suspended in 30.2 kg of heptanes, afforded a stirrable slurry that was aged for 10 min. An additional 459 kg of heptanes was added over 40 minutes. The resulting slurry was cooled to 20° C. over 2 hours and aged overnight. The slurry was subjected to wet-milling for about 60 minutes to afford a slurry with 90% of the particle less than 54 μm.

The solids were isolated in two loads by centrifuge and conical dryer or by filter dryer. The first load was washed successively with 158 kg of 4:1 heptanes/EtOAc and 143.4 kg of heptanes, before being transferred to a conical dryer. The second load was washed successively with 149 kg of 4:1 heptanes/EtOAc and 143.1 kg of heptanes, before being transferred to the same conical dryer. The resulting wet cake dried at 50° C. under vacuum in a conical dryer to afford 130.1 kg of Compound I (75% yield). 12.9 kg (8%) are lost to the mother liquor and approximately an additional 17 kg (10%) heel is expected to be left in the dryer.

What is claimed is:

1. A process for the preparation of Compound I of the formula (I)

comprising the steps of a) reacting Compound A of the formula

Compound A with a methylating agent in a suitable solvent to afford Compound B of the formula Compound B b) which is reacted in a continuous oxidation followed by a quench reaction to prepare Compound C of the formula Compound C and protecting to convert Compound C to Compound D of the formula

Compound D c) chlorinating Compound D to afford Compound E of the formula

Compound E d) which is coupled with Compound F of the formula

Compound F to afford Compound G of the formula, which is optionally crystallized to improve quality, and Compound G e) which is subsequently deprotected and reacted with (R)-(+)-propylene oxide in a suitable solvent, and optionally recrystallized to improve quality, to afford Compound H of the formula Compound H f) which is reacted with a Cbz-L-alanine and a coupling agent to afford Compound J of the formula Compound J g) which is deprotected and crystallized to afford crystalline Compound I.

2. A continuous reaction process for the preparation of Compound C of the formula Compound C from Compound B of the formula Compound B comprising oxidation of Compound B in a continuous reactor through which a solution of Compound B and hydrogen peroxide and an acid, while being cooled, are contacted as they continuously flow through the reactor.

3. The process according to claim 2 wherein Compound C, which is not isolated, is protected with pivaloyl chloride and a base to afford Compound D.

4. The process according to claim 2 wherein the continuous reaction process involves running the reaction through a low temperature zone and a high temperature zone strictly controlled to avoid thermal runaway.

5. The process according to claim 4 wherein the temperature of the reactants in the low temperature zone is kept in a range of about 0-5° C.

6. The process according to claim 4 wherein the temperature of the reactants in the high temperature zone is kept in a range of about 12-18° C.

7. The process according to claim 2 wherein the reaction stream is quenched with a reducing agent and the pH adjusted.

8. The process according to claim 7 wherein the reducing agent used is sodium bisulfite.

9. The process according to claim 2 wherein the acid used is methanesulfonic acid.

10. The process according to claim 7 wherein the quench pH is continually adjusted between 6.3 and 8.5 using ammonia.

11. The process according to claim 1 wherein Compound H is reacted with Cbz-L-alanine in the presence of THF or ethyl acetate and a coupling agent at −5 to 5° C. to afford Compound J, which is then deprotected to afford Compound I.

12. The process according to claim 11 wherein the coupling agent is EDAC-HCl.

13. The process according to claim 1 wherein Compound I is crystallized from ethyl acetate/heptanes or butyl acetate/heptanes.

14. The process according to claim 1 wherein in step e) NaOMe in acetonitrile and (R)-(+)-propylene oxide in water, is used to afford Compound H.

15. The process according to claim 14 wherein Compound G is deprotected and then reacted with propylene oxide to afford Compound H.

16. The process according to claim 14 wherein Compound H is optionally recrystallized using acetone and water.

* * * * *

UNITED STATES PATENT AND TRADEMARK OFFICE
CERTIFICATE OF CORRECTION

| | | |
|---|---|---|
| PATENT NO. | : 7,671,199 B2 | Page 1 of 1 |
| APPLICATION NO. | : 11/737787 | |
| DATED | : March 2, 2010 | |
| INVENTOR(S) | : Crispino et al. | |

It is certified that error appears in the above-identified patent and that said Letters Patent is hereby corrected as shown below:

<u>Title Page, Item (73), Assignee:</u>

Delete "Britsol-Myers Squibb Company," and insert -- Bristol-Myers Squibb Company, --

Signed and Sealed this
Twelfth Day of April, 2011

David J. Kappos
*Director of the United States Patent and Trademark Office*

UNITED STATES PATENT AND TRADEMARK OFFICE
CERTIFICATE OF CORRECTION

PATENT NO.        : 7,671,199 B2                     Page 1 of 1
APPLICATION NO.   : 11/737787
DATED             : March 2, 2010
INVENTOR(S)       : G. Crispino et al.

It is certified that error appears in the above-identified patent and that said Letters Patent is hereby corrected as shown below:

In Column 9, Line 58:
Replace "(-5C to 5C)." with -- (-5°C to 5°C). --

In Column 17, Line 6 -7:
Delete "Structure of Compound H was Cut off Funny in the Copy You Sent"

Signed and Sealed this
Eleventh Day of October, 2011

David J. Kappos
*Director of the United States Patent and Trademark Office*